(12) United States Patent
Yoshimura et al.

(10) Patent No.: US 10,784,231 B2
(45) Date of Patent: Sep. 22, 2020

(54) SEMICONDUCTOR SENSOR CHIP, SEMICONDUCTOR SENSOR CHIP ARRAY, AND ULTRASOUND DIAGNOSTIC APPARATUS

(71) Applicant: HITACHI, LTD., Tokyo (JP)

(72) Inventors: Yasuhiro Yoshimura, Tokyo (JP); Akifumi Sako, Tokyo (JP); Naoaki Yamashita, Tokyo (JP); Tatsuya Nagata, Tokyo (JP)

(73) Assignee: HITACHI, LTD., Tokyo (JP)

( * ) Notice: Subject to any disclaimer, the term of this patent is extended or adjusted under 35 U.S.C. 154(b) by 58 days.

(21) Appl. No.: 16/310,828

(22) PCT Filed: Jun. 20, 2017

(86) PCT No.: PCT/JP2017/022614
§ 371 (c)(1),
(2) Date: Dec. 18, 2018

(87) PCT Pub. No.: WO2018/012214
PCT Pub. Date: Jan. 18, 2018

(65) Prior Publication Data
US 2020/0098726 A1    Mar. 26, 2020

(30) Foreign Application Priority Data
Jul. 14, 2016   (JP) ................. 2016-139048

(51) Int. Cl.
*H01L 23/34*  (2006.01)
*H01L 25/065* (2006.01)
(Continued)

(52) U.S. Cl.
CPC ........ *H01L 25/0655* (2013.01); *B06B 1/0292* (2013.01); *H01L 24/20* (2013.01); *H01L 24/45* (2013.01)

(58) Field of Classification Search
CPC ... H01L 23/49575; H01L 24/20; H01L 24/45; H01L 24/48; H01L 24/85; H01L 25/0655; B06B 1/0292
(Continued)

(56) References Cited

U.S. PATENT DOCUMENTS

2010/0255623 A1   10/2010  Huang
2011/0086443 A1   4/2011   Kobayashi et al.
(Continued)

FOREIGN PATENT DOCUMENTS

JP    2011-523544 A    8/2011
JP    2012-169793 A    9/2012
(Continued)

OTHER PUBLICATIONS

International Search Report of PCT/JP2017/022614 dated Sep. 19, 2017.

*Primary Examiner* — Brook Kebede
(74) *Attorney, Agent, or Firm* — Mattingly & Malur, PC

(57) ABSTRACT

The present invention addresses the problem of enlarging a sensing area in an ultrasonic probe so as to achieve a higher definition. This ultrasonic diagnostic equipment is provided with an ultrasonic probe that comprises: a CMUT chip (2a) that has drive electrodes (3e)-(3j), etc., arranged in a grid-like configuration on a rectangular CMUT element section (21); and a CMUT chip (2b) that has drive electrodes (3p)-(3u), etc., arranged in a grid-like configuration on the rectangular CMUT element section (21), that is adjacent to the CMUT chip (2a), and in which the drive electrodes (3e)-(3j) of the adjacent CMUT chip (2a) are electrically connected to the respective drive electrodes (3p)-(3u) via bonding wires (4f)-(4i), etc.

8 Claims, 13 Drawing Sheets

(51) Int. Cl.
    *B06B 1/02*       (2006.01)
    *H01L 23/00*      (2006.01)
(58) Field of Classification Search
    USPC .......................................... 257/673, 726, 737
    See application file for complete search history.

(56)               References Cited

U.S. PATENT DOCUMENTS

2012/0133001  A1*   5/2012  Tkaczyk ................. H01L 27/20
                                                        257/414
2013/0172750  A1    7/2013  Yoshimura et al.
2013/0175677  A1*   7/2013  Chang .................... H01L 24/48
                                                        257/673
2013/0313663  A1   11/2013  Kato et al.
2014/0355381  A1   12/2014  Lal et al.

FOREIGN PATENT DOCUMENTS

JP         2017-148258  A     8/2017
WO         2009/154091  A1   12/2009
WO         2012/023619  A1    2/2012

* cited by examiner

[Fig. 1]
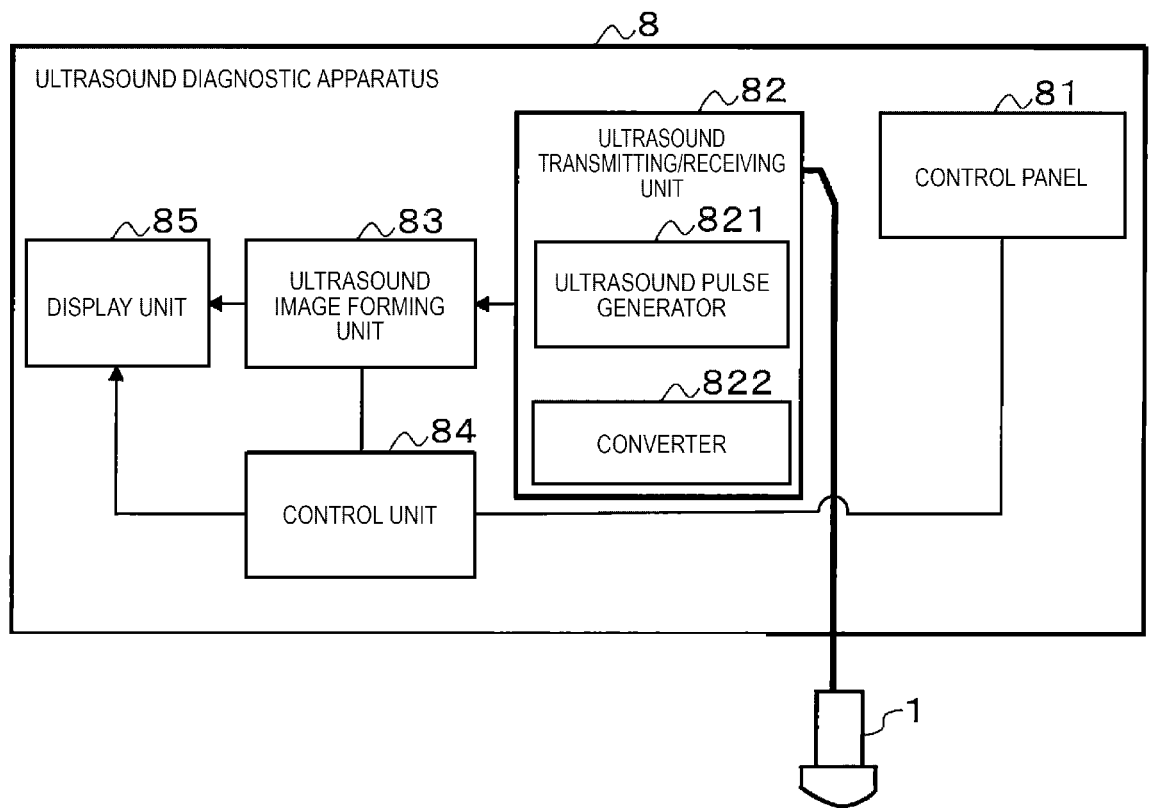
[Fig. 2]
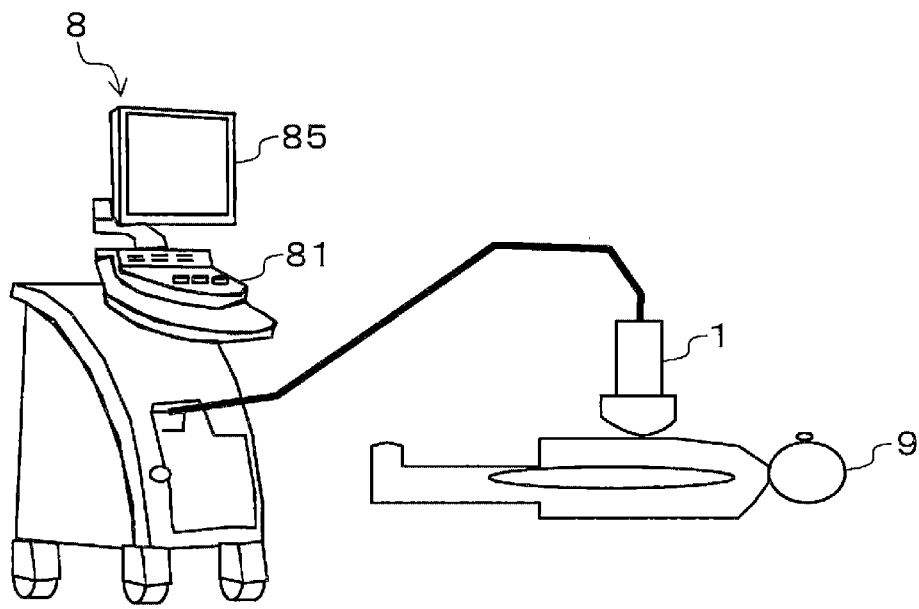

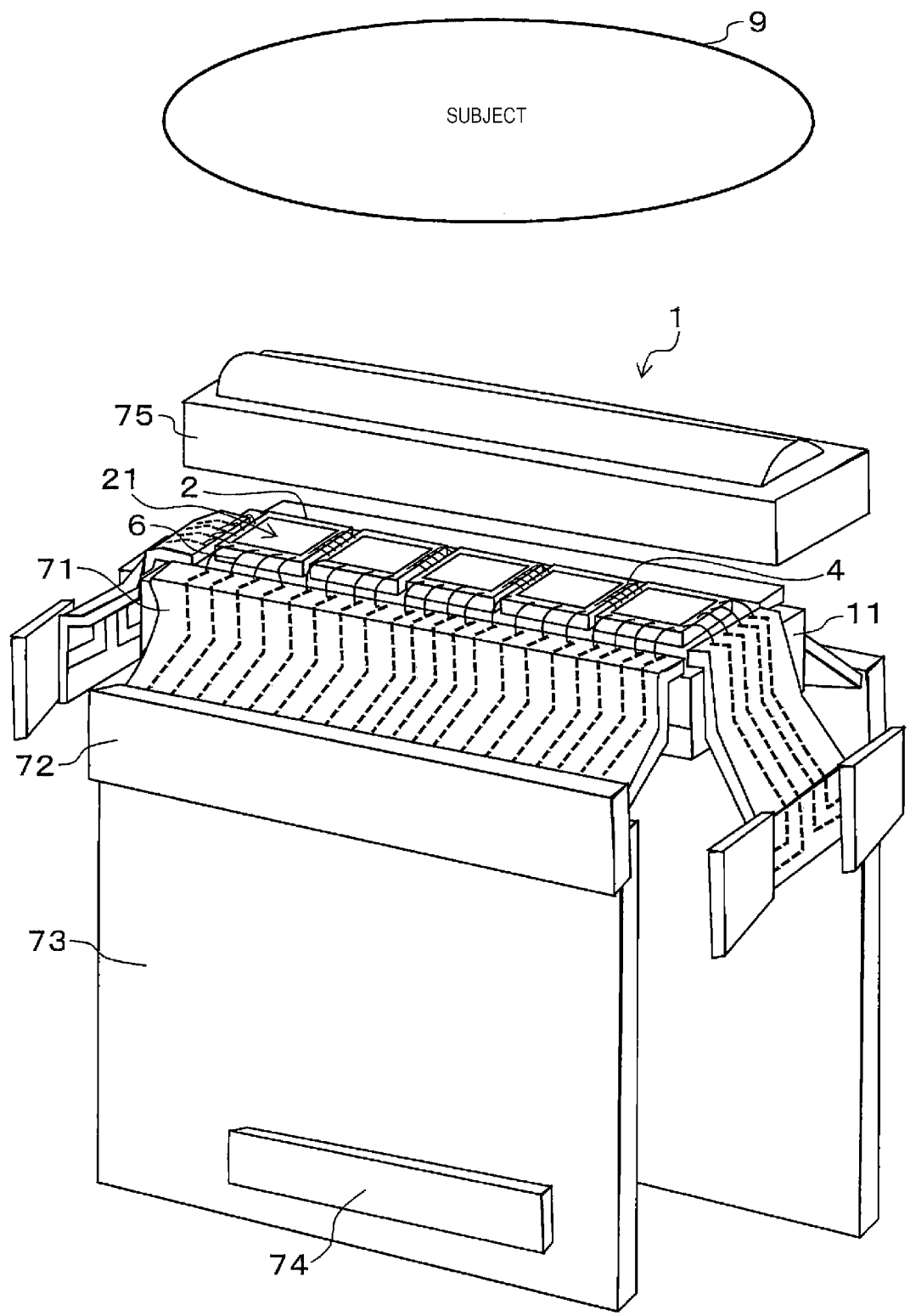
[Fig. 3]

[Fig. 4]
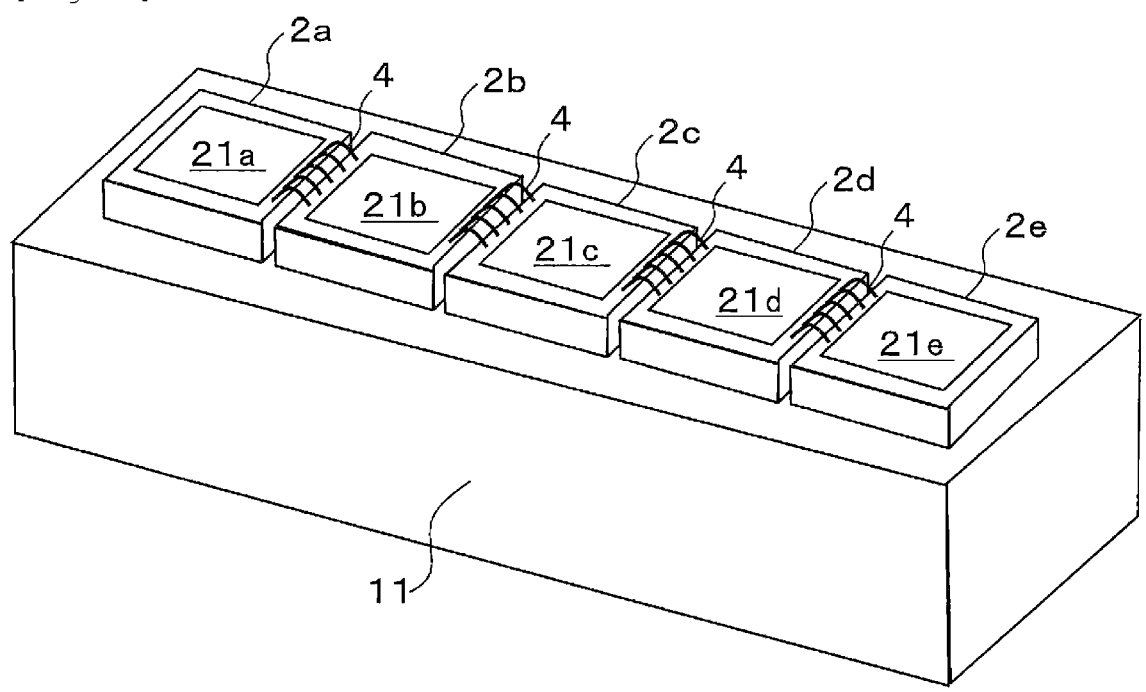

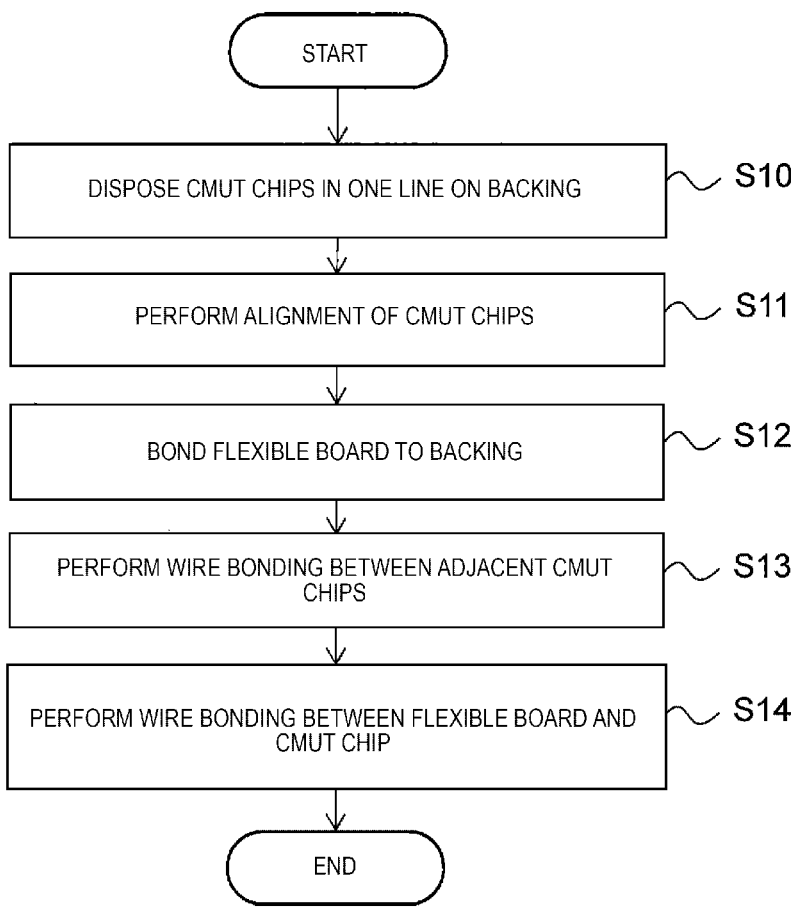
[Fig. 5]

[Fig. 6]
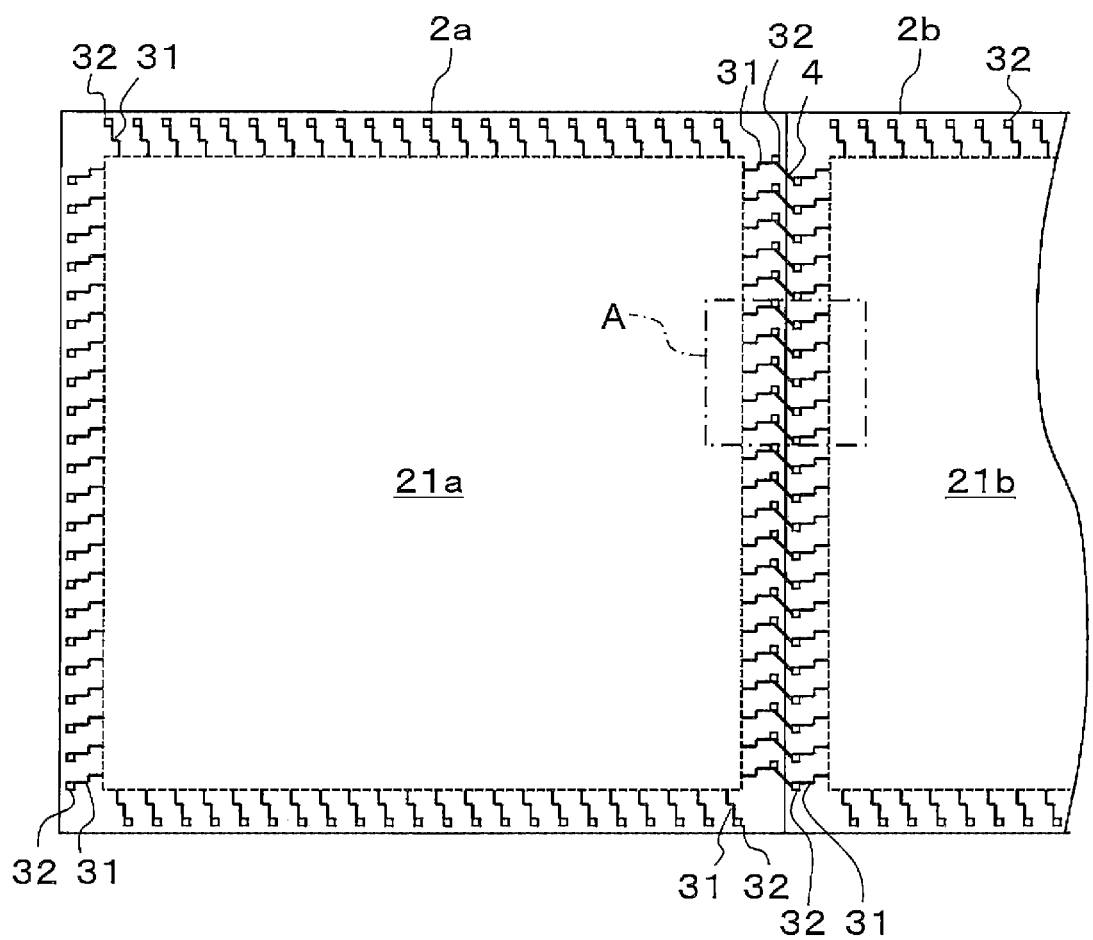

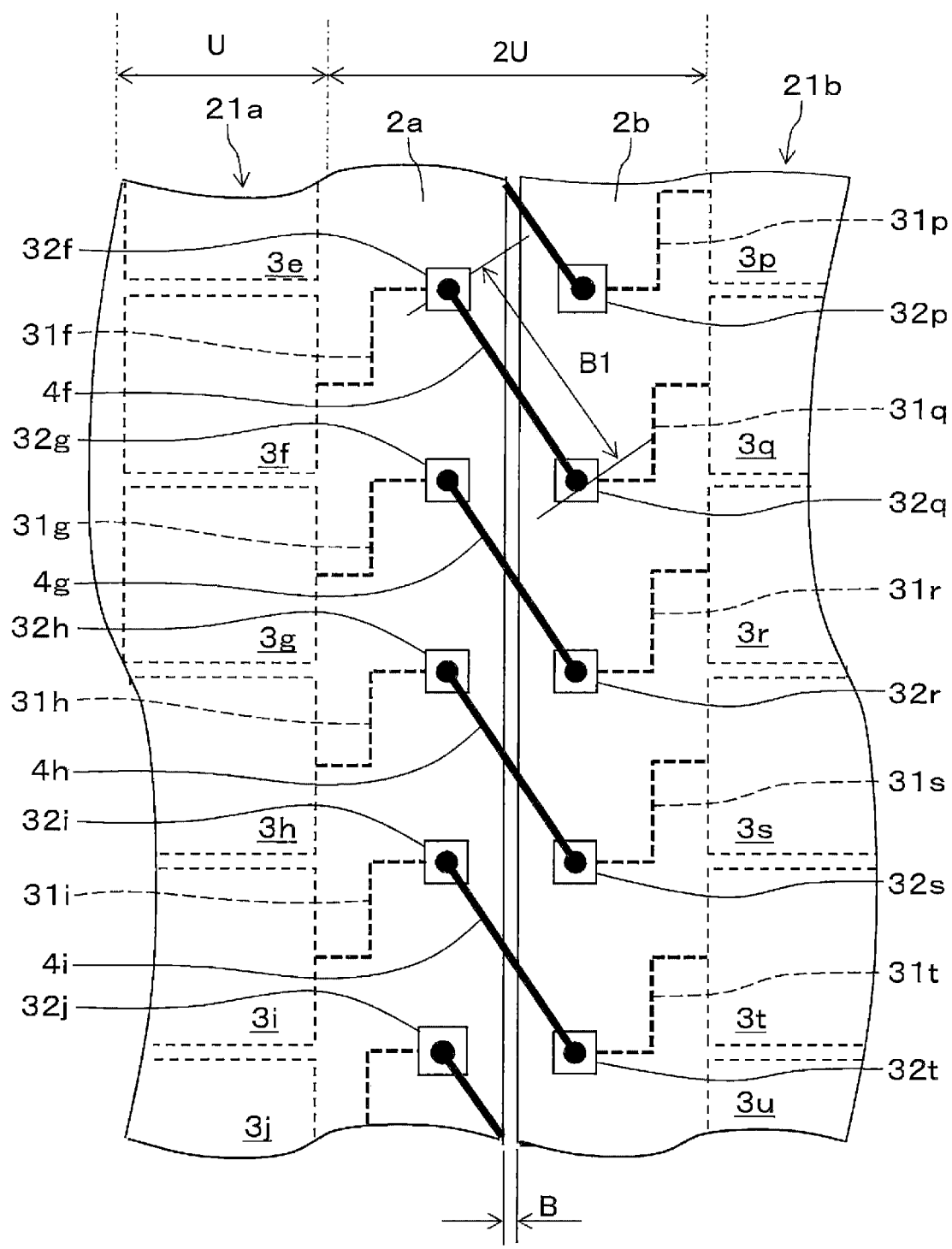
[Fig. 7]

[Fig. 8]
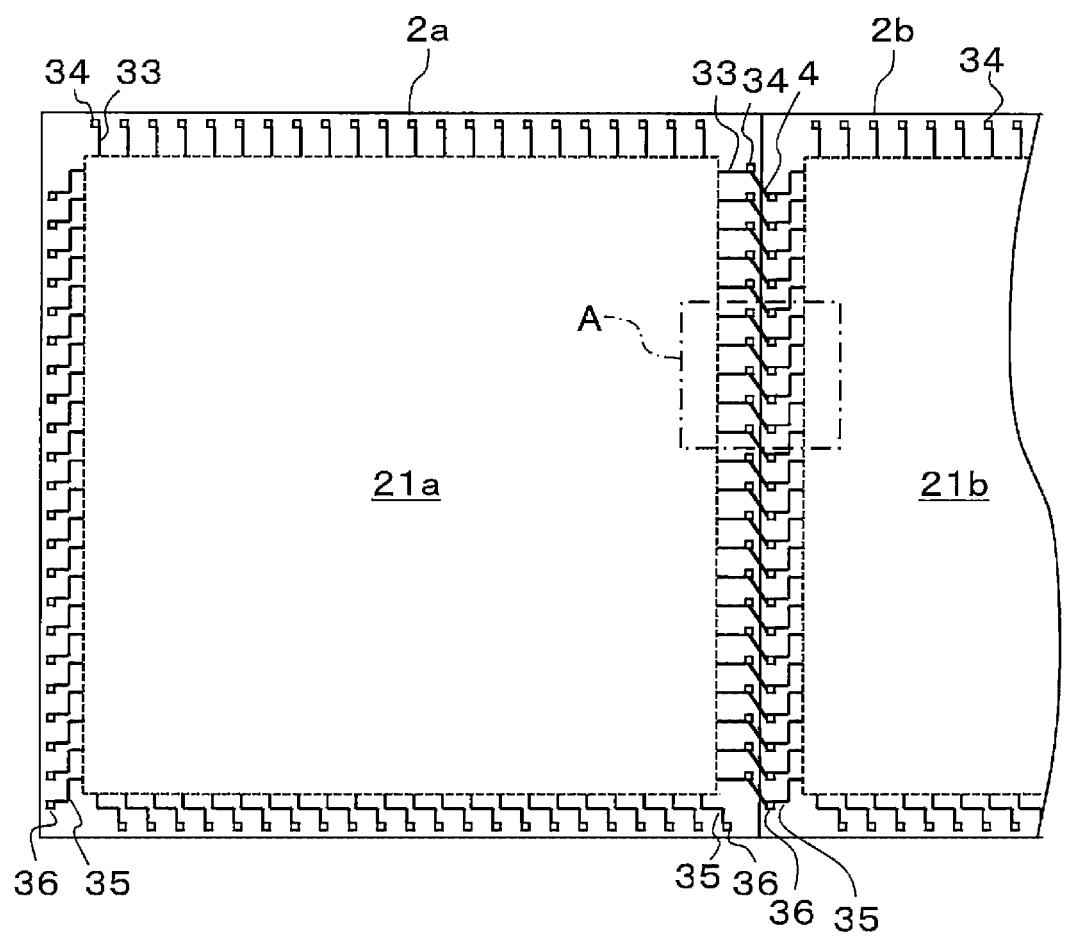

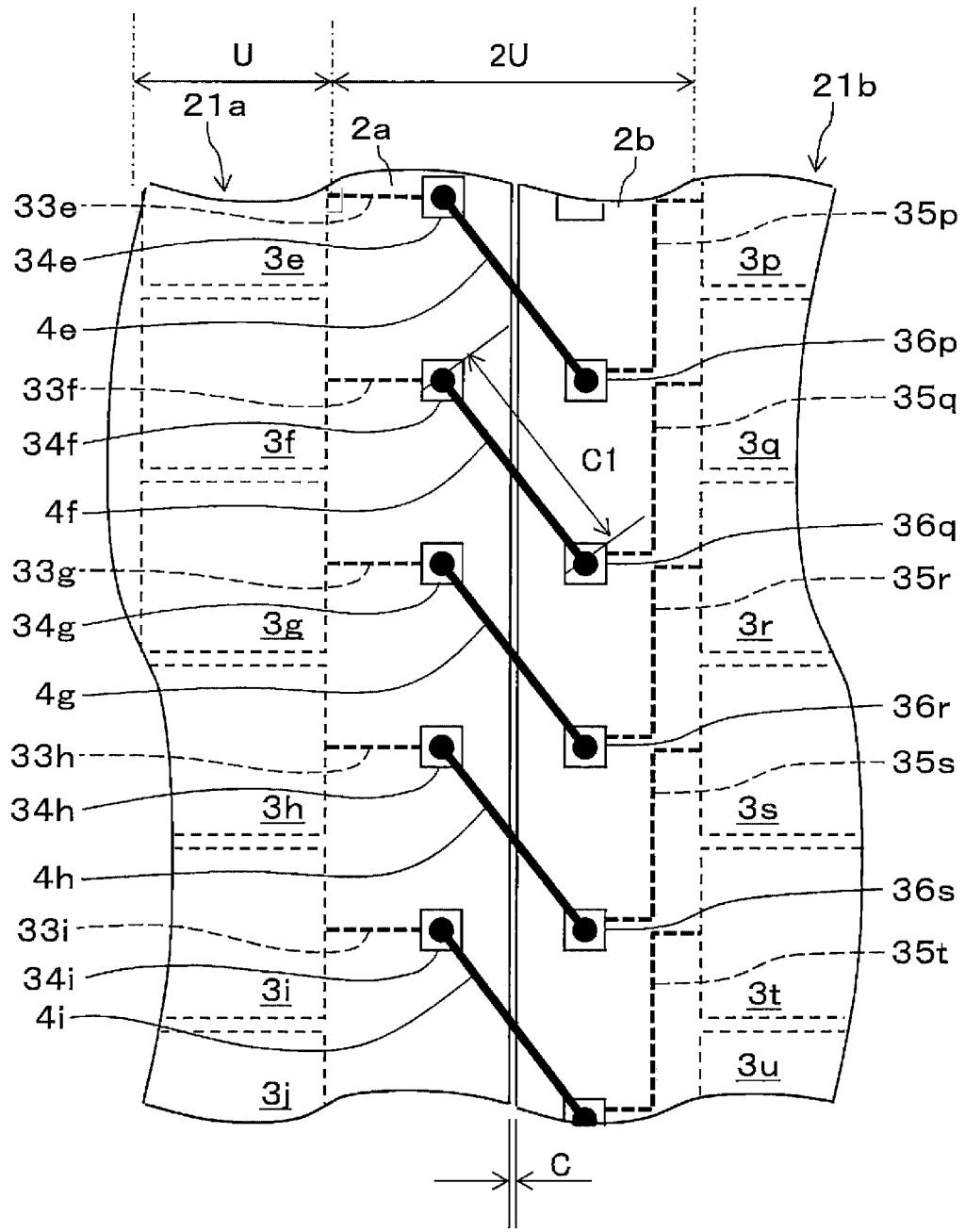
[Fig. 9]

[Fig. 10]
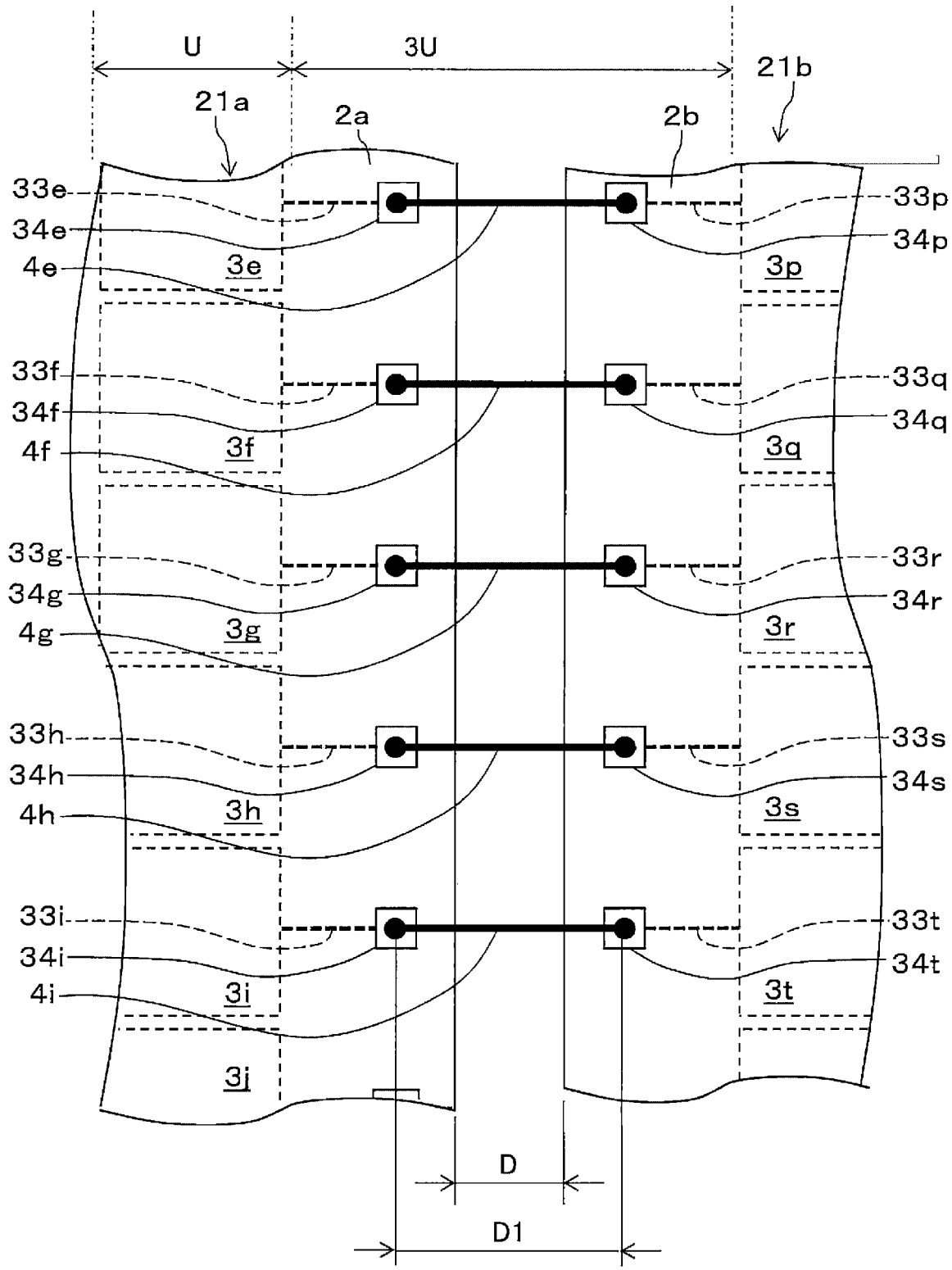

[Fig. 11]
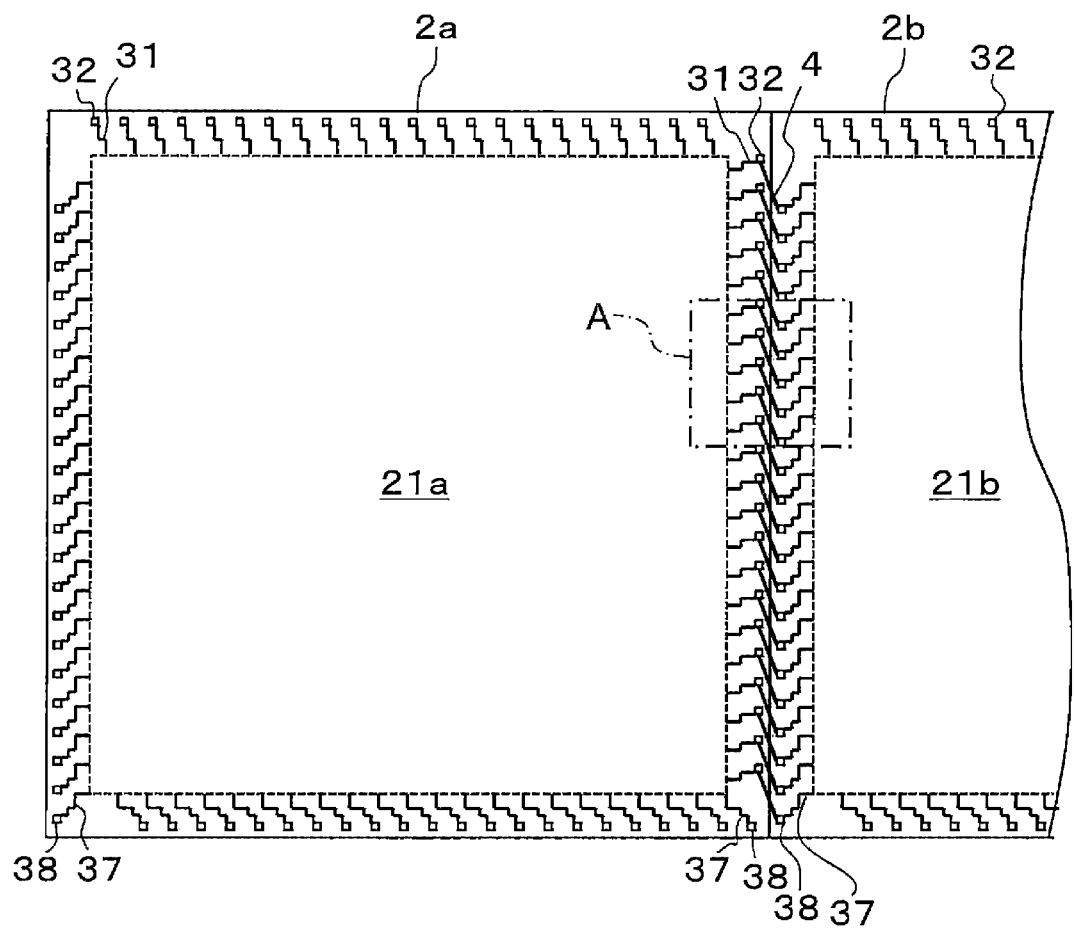

[Fig. 12]
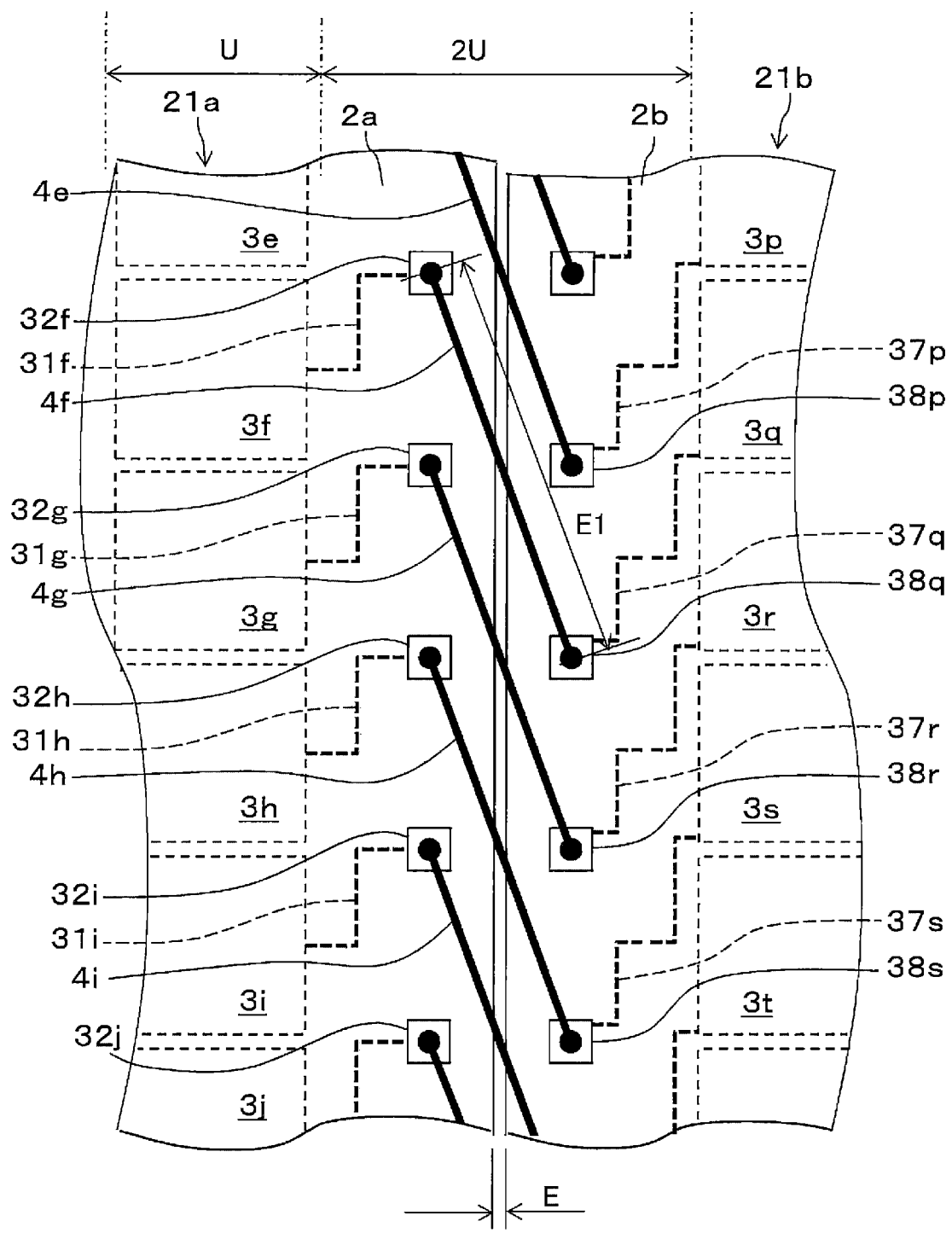

[Fig. 13]
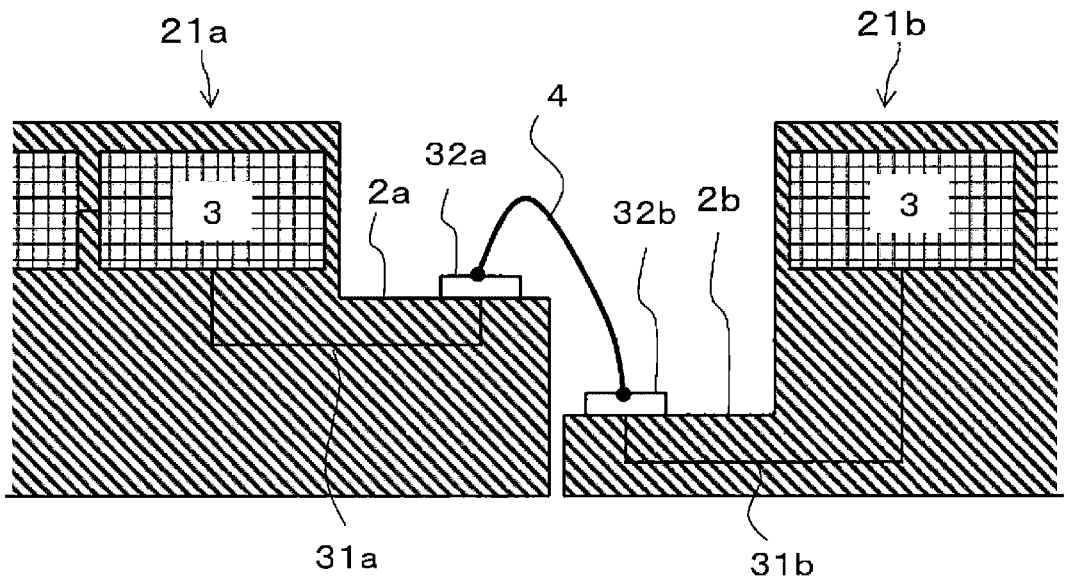
[Fig. 14]
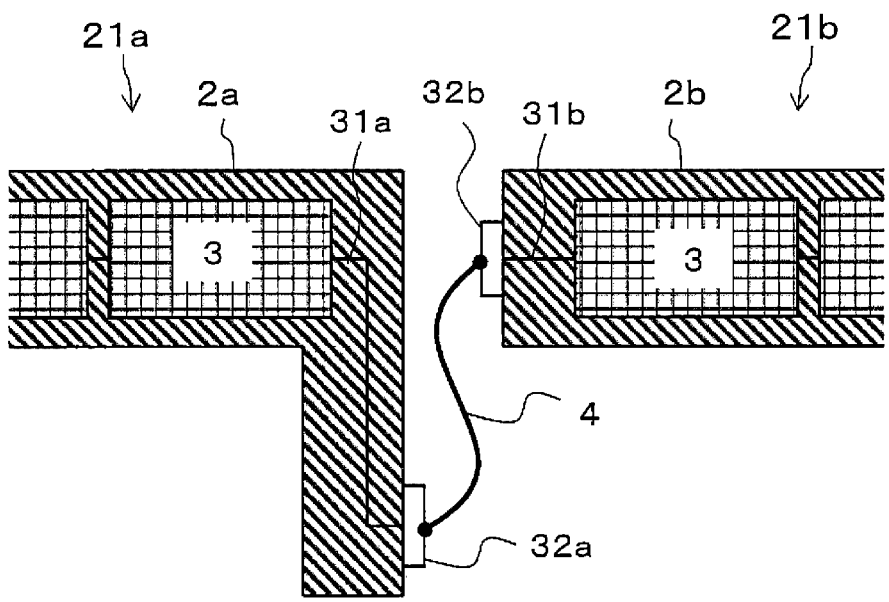

[Fig. 15]
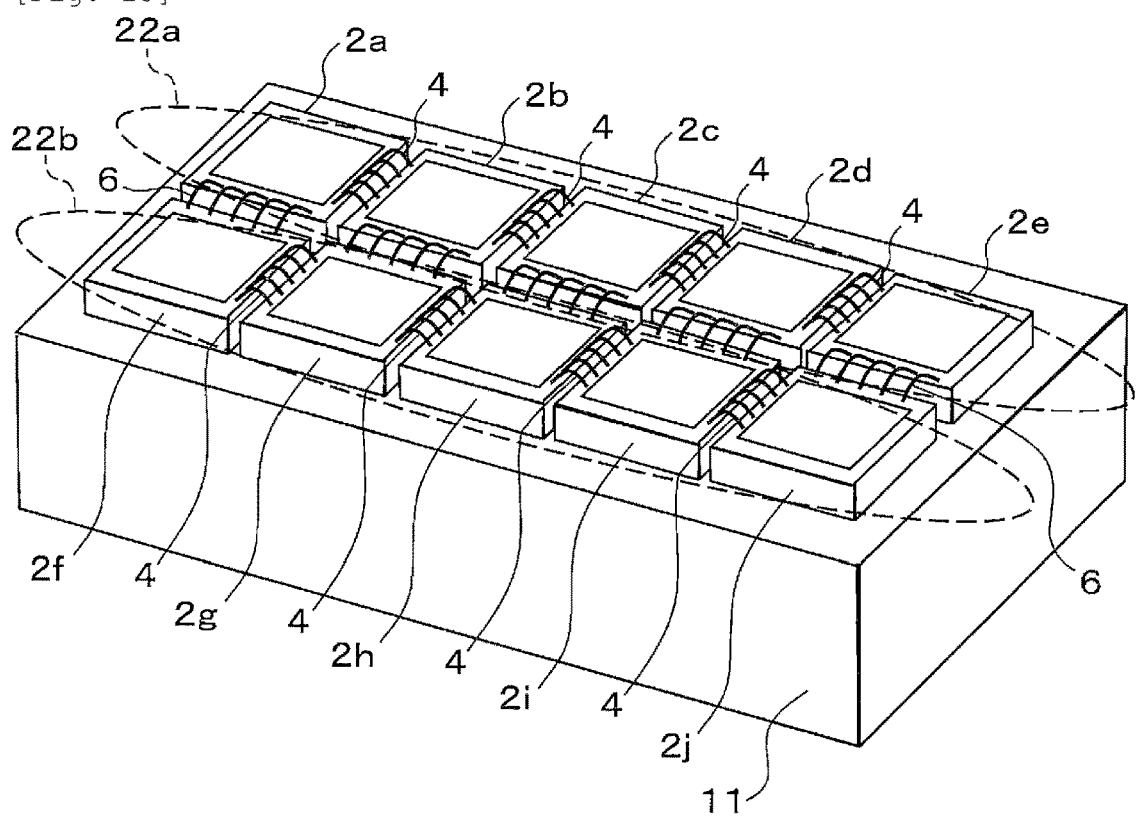
[Fig. 16]
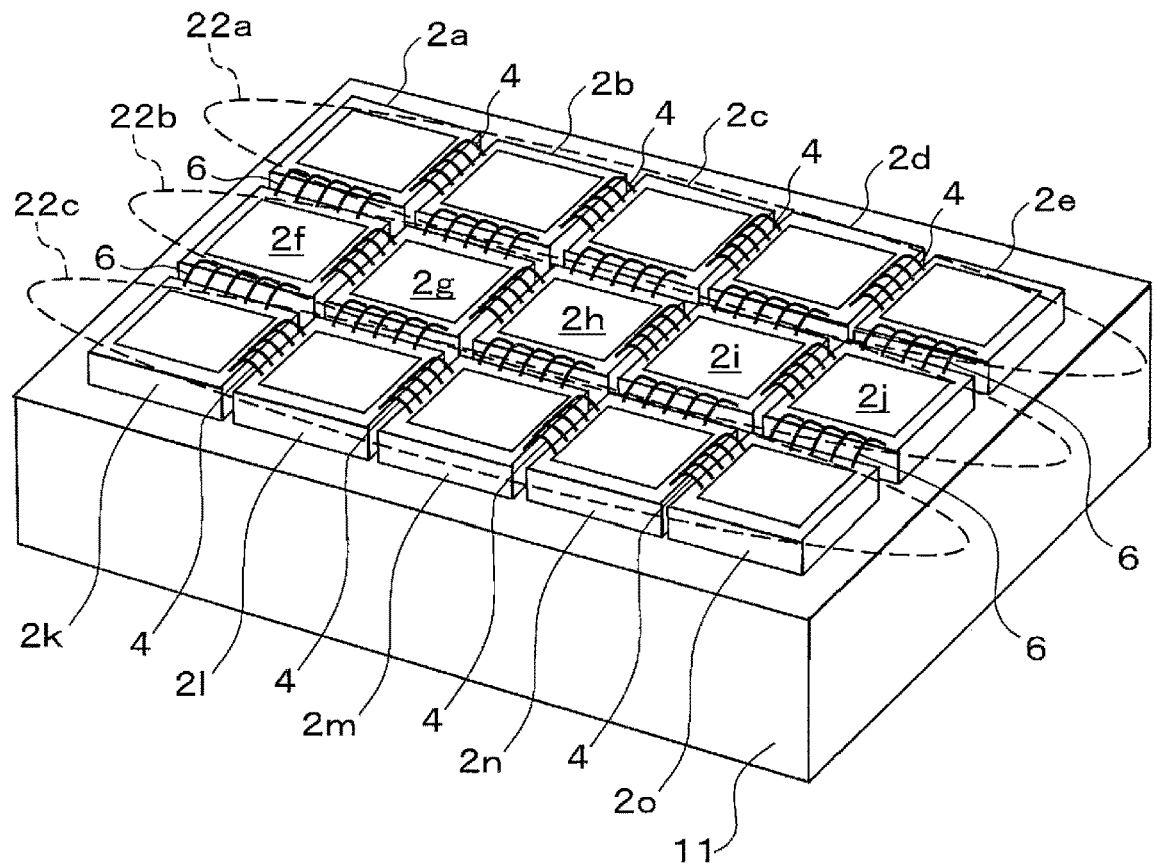

SEMICONDUCTOR SENSOR CHIP, SEMICONDUCTOR SENSOR CHIP ARRAY, AND ULTRASOUND DIAGNOSTIC APPARATUS

TECHNICAL FIELD

The present invention relates to a semiconductor sensor, a semiconductor sensor chip array, and an ultrasound diagnostic apparatus using the same.

BACKGROUND ART

An ultrasound element transmits an electric signal via a power feeding wiring or a signal wiring which is connected to the outside from the element.

Abstract in PTL 1 provides the following description. "Embodiments of a method for packaging cMUT arrays allow packaging multiple cMUT arrays on the same packaging substrate introduced over a side of the cMUT arrays. The packaging substrate is a dielectric layer on which openings are patterned for depositing a conductive layer to connect a cMUT array to I/O pads interfacing with external devices. Auxiliary system components may be packaged together with the cMUT arrays. Multiple cMUT arrays and optionally multiple auxiliary system components can be held in place by a larger support structure for batch production. The support structure can be made of an arbitrary size using inexpensive materials."

CITATION LIST

Patent Literature

PTL 1: JP-T-2011-523544

SUMMARY OF INVENTION

Technical Problem

A capacitive micro-machined ultrasonic transducer (CMUT) chip is an ultrasound transmitting/receiving devices produced by laminating thin films. The CMUT chip is produced by applying a semiconductor manufacturing technology and a microelectromechanical system (MEMS) technology. Since it is possible to form elements collectively in a grid shape by the semiconductor manufacturing technology, the multiple elements arranged in the grid shape are cut out from a semiconductor wafer, and the CMUT chip is packaged as one chip.

On the other hand, as for an ultrasound sensor, there is a demand for a sensor that performs sensing over a large area in high definition. Examples of the sensor include a tactile sensor or a touch sensor that simulates a human hand, an ultrasound flow detector that is capable of performing detection over a large area at once, a probe for an ultrasound diagnostic apparatus that is used for a medical diagnosis of a human or an animal, or the like. In addition, a semiconductor sensor as an optical sensor such as a complementary metal oxide semiconductor sensor (CMOS sensor) is used for a video camera or a digital camera. The semiconductor sensor having a sensing portion with a large area enables high definition (high resolution) to be realized.

In the semiconductor manufacturing technology, a yield ratio of the chips decreases due to foreign matter during a wafer process or a photolithography defect. The foreign matter or the defect is specific to a manufacturing line, and thus the yield ratio decreases as a chip has a large area and the number of chips acquired for each wafer is reduced. Regarding economic efficiency, if the yield ratio of the chip acquisition is to reach a predetermined value or higher, an area of the semiconductor sensor is restricted.

In order to increase the area of the semiconductor sensor while the yield ratio of the chip acquisition reaches the predetermined value or higher, it is effective to arrange a plurality of small semiconductor chips. In this case, a problem arises in a method of electrically connecting the plurality of semiconductor chips.

The present invention has an object to provide semiconductor sensor chips which are connectable to each other, a semiconductor sensor chip array that has an increased sensing area so as to achieve high definition, and an ultrasound diagnostic apparatus.

Solution to Problem

In order to solve the problem described above, an ultrasound diagnostic apparatus according to the present invention includes an ultrasound probe that includes a first semiconductor sensor chip that is provided with an element portion in which sensor cells are arranged, and a second semiconductor sensor chip that is provided with an element portion in which sensor cells are arranged, that is adjacent to the first semiconductor sensor chip, and that has an electric connection via a bonding wire between each of the sensor cells and an adjacent sensor cell of the first semiconductor sensor chip.

The other means will be described in embodiments of the invention.

Advantageous Effects of Invention

According to the present invention, it is possible to provide semiconductor sensor chips which are connectable to each other, a semiconductor sensor chip array that has an increased sensing area so as to achieve high definition, and an ultrasound diagnostic apparatus.

BRIEF DESCRIPTION OF DRAWINGS

FIG. 1 is a block diagram showing a configuration of an ultrasound diagnostic apparatus and an ultrasound probe.

FIG. 2 is a diagram showing the external appearance of the ultrasound diagnostic apparatus and the ultrasound probe.

FIG. 3 is a diagram showing a schematic configuration of the ultrasound probe.

FIG. 4 is a perspective view in the vicinity of CMUT chips arranged in five columns.

FIG. 5 is a flowchart showing a method for manufacturing the ultrasound probe.

FIG. 6 is a top view of a region in which CMUT chips are adjacent to each other in a first embodiment.

FIG. 7 is an enlarged top view of a region in which the CMUT chips are adjacent to each other in the first embodiment.

FIG. 8 is a top view of a region in which CMUT chips are adjacent to each other in a second embodiment.

FIG. 9 is an enlarged top view of a region in which the CMUT chips are adjacent to each other in the second embodiment.

FIG. 10 is an enlarged top view of a region in which CMUT chips are adjacent to each other in a third embodiment.

FIG. 11 is a top view of a region in which CMUT chips are adjacent to each other in a fourth embodiment.

FIG. 12 is an enlarged top view of a region in which the CMUT chips are adjacent to each other in the fourth embodiment.

FIG. 13 is an enlarged sectional view of a region in which CMUT chips are adjacent to each other in a fifth embodiment.

FIG. 14 is an enlarged sectional view of a region in which CMUT chips are adjacent to each other in a sixth embodiment.

FIG. 15 is a perspective view in the vicinity of CMUT chips arranged in a grid shape with two rows and five columns in a seventh embodiment.

FIG. 16 is a perspective view in the vicinity of CMUT chips arranged in a grid shape with three rows and five columns in an eighth embodiment.

DESCRIPTION OF EMBODIMENTS

Hereinafter, embodiments of the present invention will be described with reference to the figures.

FIG. 1 is a block diagram showing a configuration of an ultrasound diagnostic apparatus 8 and an ultrasound probe 1.

The ultrasound diagnostic apparatus 8 forms and displays a two-dimensional ultrasound image, a three-dimensional ultrasound image, or various types of Doppler images of a diagnostic site by using an echo signal obtained by transmitting ultrasound into a subject 9 and receiving the ultrasound. Specifically, the ultrasound diagnostic apparatus 8 is configured to include an ultrasound transmitting/receiving unit 82, an ultrasound image forming unit 83, a display unit 85, a control unit 84, and a control panel 81. The ultrasound probe 1 is electrically connected to the ultrasound transmitting/receiving unit 82.

The ultrasound probe 1 transmits the ultrasound to the subject 9 and receives reflected echo. A CMUT chip is mounted on the ultrasound probe 1. The CMUT chip is an ultrasound transmitting/receiving device produced by laminating thin films in application of a semiconductor manufacturing technology and a microelectromechanical system (MEMS) technology.

The ultrasound transmitting/receiving unit 82 generates an electric signal having a pulse shape for generating an ultrasound signal that is transmitted to the subject 9. The ultrasound transmitting/receiving unit 82 includes an ultrasound pulse generator 821, which transmits the generated electric signal to the ultrasound probe 1, and a converter 822, which converts an echo signal received by the ultrasound probe into an electric signal. The ultrasound transmitting/receiving unit 82 may be any commercially available ultrasound transceiver or the like, for example.

The ultrasound image forming unit 83 forms a two-dimensional ultrasound image, a three-dimensional ultrasound image, or various types of Doppler images from a received signal. Specifically, the ultrasound image forming unit 83 is configured of a central processing unit (CPU) or the like, for example.

The display unit 85 displays the ultrasound image formed by the ultrasound image forming unit 83. In addition, on the display unit 85, information input by the control panel 81 to be described below, other information necessary for a diagnosis, or the like are together displayed. Specifically, the display unit 85 is configured of a liquid crystal display (LCD), a monitor device, or the like.

The control unit 84 controls every means based on control information that is input through the control panel 81 to be described below. Specifically, the control unit 84 is configured of the CPU or the like.

The control panel 81 is used for inputting any item of information by an operator such that the operator conducts a desired diagnosis on the subject 9. The control unit 84 controls every means based on the input information. Specifically, the control panel 81 is configured to have a push button, a touch panel, or the like.

FIG. 2 is a diagram showing the external appearance of the ultrasound diagnostic apparatus 8 and the ultrasound probe 1.

A state in which the ultrasound diagnostic apparatus 8 and the ultrasound probe 1 are specifically applied to the subject 9 is described.

An operator inputs a diagnosis condition by the control panel 81 and scans the subject 9, which is a human body, by using the ultrasound probe 1.

The ultrasound probe 1 is electrically connected to the ultrasound diagnostic apparatus 8 via a cable or the like so as to transmit an ultrasound signal to the subject 9, which is a human body, and receive the ultrasound signal reflected as an echo from the subject 9. The received ultrasound signal is converted into an ultrasound image by the ultrasound diagnostic apparatus 8 and is displayed on the display unit 85. Consequently, it is possible to make an inside of the subject 9 visible and conduct the diagnosis.

FIG. 3 is a diagram showing a schematic configuration of the ultrasound probe 1.

As shown in FIG. 3, the ultrasound probe 1 includes a plurality of CMUT chips 2 at a distal end of a backing 11. The CMUT chip 2 irradiates the subject 9 via an acoustic lens 75 with ultrasound and receives ultrasound reflected from the subject 9. Details of this will be described below. The CMUT chip 2 is connected, via a bonding wire 6, to a flexible board 71 having a wiring that is connected to a connector 72. The connector 72 is connected to a circuit board 73. A connection terminal 74 on the circuit board 73 is connected to the ultrasound diagnostic apparatus 8 (refer to FIG. 1).

The ultrasound diagnostic apparatus 8 (refer to FIG. 2) imparts the electric signal to the CMUT chip 2 so as to vibrate the chip and forms an image based on the signal received from the subject 9. On a surface of the CMUT chip 2, the silicone resin acoustic lens 75 for causing the ultrasound generated from the CMUT chip 2 to focus on a direction of the subject 9 is provided. The CMUT chip 2 transmits and receives the ultrasound to and from the subject 9, which is the human body, through the acoustic lens 75.

FIG. 4 is a perspective view in the vicinity of CMUT chips 2a to 2e arranged in five columns.

A configuration in the vicinity of the plurality of CMUT chips 2a to 2e of the ultrasound probe 1 is described in detail. The five columns of CMUT chips 2a to 2e are disposed in one line on the backing 11 and adhere to the backing 11. For example, adhesion is performed by using a sheet-shaped adhesive. The CMUT chips 2a to 2e include rectangular CMUT element portions 21a to 21e inside, respectively. The CMUT element portions 21a to 21e each have drive electrodes which function as sensor cells and are disposed in a grid shape. The CMUT chips 2a to 2e have pads (refer to FIG. 6) for connecting to the outside of the CMUT chip 2a, the pads provided on an outer side of the CMUT element portions 21a to 21e.

The pad of the CMUT chip 2a is electrically connected to the pad (refer to FIG. 6) of the CMUT chip 2b adjacent to the CMUT chip 2a in a column direction via a bonding wire 4. The pad of the CMUT chip 2b is electrically connected to the pad of the CMUT chip 2c adjacent to the CMUT chip 2b in the column direction via the bonding wire 4. The pad of the CMUT chip 2c is electrically connected to the pad of the CMUT chip 2d adjacent to the CMUT chip 2c in the column direction via the bonding wire 4. The pad of the CMUT chip 2d is electrically connected to the pad of the CMUT chip 2e adjacent to the CMUT chip 2d in the column direction via the bonding wire 4.

FIG. 5 is a flowchart showing a method for manufacturing the ultrasound probe 1. Manufacturing equipment (not shown) performs the manufacturing method.

First, the manufacturing equipment disposes the CMUT chips 2a to 2e in one line on the backing 11 (Step S10) and performs alignment of the CMUT chips 2a to 2e (Step S11). When the manufacturing equipment bonds the flexible board 71 to the backing 11 (Step S12), the manufacturing equipment performs wire bonding of the adjacent CMUT chips 2 to each other (Step S13). The manufacturing equipment performs wire bonding between the flexible board 71 and the CMUT chips 2a to 2e (Step S14). Consequently, a part of the ultrasound probe 1 as shown in FIG. 3 is configured.

First Embodiment

FIG. 6 is a top view of a region in which the CMUT chips 2a and 2b are adjacent to each other in the first embodiment.

The top view in FIG. 6 shows a relationship between the CMUT chips 2a and 2b, which are adjacent to each other in the column direction, pads 32, and the bonding wires 4. The CMUT chip 2a has a rectangular shape and includes the CMUT element portion 21a on an inner side thereof, and the pads 32 for providing an electrical connection to the outside are disposed on a peripheral portion of the CMUT element portion. The pad 32 is electrically connected to the CMUT element portion 21a via a crank-shaped internal wiring 31. The crank-shaped internal wiring 31 is wired to be oblique with respect to each side of the CMUT chip 2a and has point symmetry to opposite sides.

In other words, the CMUT chips 2 each have a readout line of a signal, which has a configuration in which a plurality of sensor cells are electrically connected to one another. A wiring to the outside of the CMUT chip 2 from sensor cells positioned on both ends of the sensor cells (drive electrodes 3) contained in the readout line is disposed at a predetermined angle with respect to a general direction in which the readout line extends. The wiring at the predetermined angle does not need to be straight and may be wired to be oblique in an upward crank shape with respect to the direction of the readout line as shown in FIG. 6.

As described above, the CMUT chips 2 are arranged, and pads 32 connected to the drive electrodes in the same column are connected to each other. In this manner, it is possible to perform sensing over a wide range at once. Further, the CMUT chips 2 are disposed in the grid shape, pads 32 connected to the drive electrodes in the same column are connected to each other, and pads 32 connected to the drive electrodes in the same row are connected to each other. Consequently, the ultrasound probe 1 is able to perform sensing over a wide range at once.

In FIGS. 6, 8, and 11, the internal wiring 31 is represented by a solid line in order to be shown clearly; however, the internal wiring 31 is not exposed to a top surface but is covered with an insulator, and thus it is not possible to visually recognize the wiring from the outside. Accordingly, in FIGS. 7, 9, 10, and 12, the internal wiring 31 is represented by a dashed line.

The CMUT chip 2b is configured similarly to the CMUT chip 2a, and pads 32 of the CMUT chip 2a and the CMUT chip 2b adjacent to the CMUT chip 2a are connected to each other via a bonding wire 4. Connection will be described in detail in FIG. 7 to be described below.

FIG. 7 is an enlarged view of a region A in which the CMUT chips 2a and 2b are adjacent to each other in the first embodiment.

In the CMUT chip 2a, drive electrodes 3e to 3j or the like for driving a membrane (not shown) are formed inside the CMUT element portion 21a. Hereinafter, the drive electrodes 3e to 3j are simply referred to as the drive electrode 3 when the drive electrodes are not particularly distinguished from each other. The drive electrodes 3 (not shown) are arranged in the grid shape inside the CMUT element portion 21a.

Similarly, in the CMUT chip 2b, drive electrodes 3p to 3u or the like for driving a membrane are formed inside the CMUT element portion 21b.

The drive electrode 3f of the CMUT chip 2a is connected to a pad 32f via an internal wiring 31f. A vertical position of the pad 32f of the paper surface is disposed between the drive electrode 3f and the drive electrode 3e adjacent to the drive electrode 3f and is disposed outside the CMUT element portion 21a that is configured to include the drive electrodes 3e to 3i. Similarly, the other drive electrodes 3g to 3i are connected to pads 32g to 32i via internal wirings 31g to 31i and are disposed similarly. Hereinafter, the internal wirings 31g to 31i or the like is simply referred to as the internal wiring 31 when the internal wirings are not specifically distinguished.

The drive electrode 3q of the CMUT chip 2b is connected to a pad 32q via an internal wiring 31q. A vertical position of the pad 32q of the paper surface is disposed between the drive electrode 3q and the drive electrode 3r adjacent to the drive electrode 3q and is disposed outside (a left side on the figure) the CMUT element portion 21b that is configured to include the drive electrodes 3p to 3u. Similarly, the other drive electrodes 3p and 3r to 3t are connected to pads 32p and 32r to 32t via internal wirings 31p and 31r to 31t and are disposed similarly.

The drive electrode 3f is electrically connected to the drive electrode 3q adjacent to the drive electrode 3f, and thus the pad 32f and the pad 32q are connected via the bonding wire 4f. The other drive electrodes 3g to 3i are electrically connected to the drive electrodes 3r to 3t adjacent to each other, and thus the pads 32g to 32i and the pads 32r to 32t are connected via the bonding wires 4g to 4i. Hereinafter, the bonding wires 4g to 4i or the like is simply referred to as the bonding wire 4 when there is no need to particularly distinguish the bonding wires.

The pad 32f is deviated to the upper side on the paper surface from the drive electrode 3f and the pad 32q is deviated to the lower side of paper surface from the drive electrode 3q. That is, the pad 32f and the pad 32q are obliquely disposed. Therefore, even when a chip gap B is narrow, it is possible to secure a length B1 of the bonding wire 4f, and thus it is possible to perform connection in a wire bonding method.

The other pads 32g to 32j are deviated to the upper side on the paper surface from the drive electrodes 3g to 3j, and positions of the pads 32p and 32r to 32t are deviated to the lower side of paper surface from the drive electrodes 3p and 3r to 3t.

It is preferable that the chip gap B between the CMUT chip 2a and the CMUT chip 2b is narrow when the ultrasound images are joined together and formed. The pad 32f is disposed in an obliquely upper right direction with respect to the drive electrode 3f and is connected to the internal wiring 31f. In addition, the pad 32q is disposed in an obliquely lower left direction with respect to the drive electrode 3q and is connected to the internal wiring 31q. Consequently, when the drive electrode 3f and the drive electrode 3q are disposed without deviation of the vertical position of the paper surface, it is possible to secure a length B1 of the bonding wire 4f, and thus the drive electrode 3f and the drive electrode 3q can be connected in the wire bonding method.

In addition, when ultrasound images are joined together and formed, it is desirable that a distance between the drive electrode 3f of the CMUT chip 2a and the drive electrode 3q of the CMUT chip 2b is an integral multiple of a width U of the drive electrode 3. In the first embodiment, as shown in FIG. 7, a distance between the drive electrode 3f of the CMUT chip 2a and the drive electrode 3q of the CMUT chip 2b is twice the width U. Here, the CMUT chips 2a and 2b are disposed to be separated by the chip gap B.

Second Embodiment

FIG. 8 is a top view of a region in which the CMUT chips 2a and 2b are adjacent to each other in the second embodiment.

The top view in FIG. 8 shows a relationship between the adjacent CMUT chips 2a and 2b, pads 34, and 36, and the bonding wires 4. The CMUT chip 2a has a rectangular shape and includes the CMUT element portion 21a inside thereof. In the CMUT chip 2a, the pad 34 for providing an electrical connection to the outside is disposed on an upper side and a right side, and the pad 36 for providing an electrical connection to the outside is disposed on a lower side and a left side. The pad 34 is electrically connected to the CMUT element portion 21a via an internal wiring 33 having a straight line shape. The pad 36 is electrically connected to the CMUT element portion 21a via a crank internal wiring 35. The crank-shaped internal wiring 35 is wired to be oblique with respect to each side of the CMUT chip 2a. The CMUT chip 2b is also configured to be similar to the CMUT chip 2a.

The pad 34 of the CMUT chip 2a and the pad 36 of the CMUT chip 2b that is adjacent to the CMUT chip 2a are connected via the bonding wire 4. Connection will be described in detail in FIG. 9 to be described below.

FIG. 9 is an enlarged top view of a region in which the CMUT chips 2a and 2b are adjacent to each other in the second embodiment.

Adjacent disposition of the CMUT chips 2a and 2b shown in FIG. 9 is similar to the first embodiment in FIG. 7. The second embodiment differs from the first embodiment in that the pad 34 included in the CMUT chip 2a and the pad 36 included in the CMUT chip 2b are disposed to be parallel to the drive electrode 3.

The pad 34f of the CMUT chip 2a is disposed sideways from the drive electrode 3f, and the pad 36q of the CMUT chip 2b is disposed sideways from the drive electrode 3r. That is, the pad 34f and the pad 36q are deviated from each other and obliquely disposed. However, the pad 36q and the drive electrode 3q are connected to each other via the internal wiring 35q, and the pad 36q and the pad 34f are electrically connected via the bonding wire 4f. Accordingly, the drive electrode 3f of the CMUT chip 2a and the drive electrode 3q of the CMUT chip 2b are electrically connected and are driven in conjunction. Similarly, the drive electrodes 3e and 3g to 3i of the CMUT chip 2a and the drive electrodes 3p and 3r to 3t of the CMUT chip 2b are electrically connected and are driven in conjunction. Hence, a line of drive electrodes 3 sideways from the CMUT chips 2a and 2b can be driven at the same time. In this case, since each bonding wires 4e to 4i have a length C1 and secure a length equal to or longer than the minimum length of the bonding wire 4f, and thus it is possible to perform connection in a wire bonding method.

In addition, when the ultrasound images are joined together and formed, it is desirable that the distance between the drive electrode 3f of the CMUT chip 2a and the drive electrode 3q of the CMUT chip 2b is an integral multiple of the width U of the drive electrode 3. In the second embodiment, as shown in FIG. 9, a distance between the drive electrode 3f of the CMUT chip 2a and the drive electrode 3q of the CMUT chip 2b is twice the width U. In this case, the CMUT chips 2a and 2b are disposed to be separated by a chip gap C.

Third Embodiment

FIG. 10 is an enlarged top view of a region in which the CMUT chips 2a and 2b are adjacent to each other in the third embodiment.

Similar to the second embodiment, pads 34e to 34i are disposed parallel to the drive electrodes 3e to 3j. Further, pads 34p to 34t are disposed to be parallel to the drive electrodes 3p to 3t. The pads 34e to 34i and the drive electrodes 3e to 3j are connected to internal wirings 33e to 33i, and the pads 34p to 34t and the drive electrodes 3p to 3t are connected to internal wirings 33p to 33t. The pads 34e to 34i and the pads 34p to 34t are connected to the bonding wires 4e to 4i, respectively. Consequently, the drive electrodes 3e to 3j and the drive electrodes 3p to 3t, which are disposed in parallel, can be electrically connected in conjunction.

Here, a relationship between a chip gap and the minimum necessary length of the bonding wire 4 is described. In the first embodiment shown in FIG. 7, the length B1 of the bonding wire 4 is set to the minimum length or longer, and thereby it is possible to set the chip gap B.

In the second embodiment shown in FIG. 9, since the length D1 of the bonding wire 4 is secured to be the minimum length or longer, the gap between the CMUT chips 2a and 2b becomes a chip gap D. Since the length B1 and the length D1 of the bonding wire 4 are equal, the chip gap D is longer than the chip gap B.

Preferably, as shown in the first and second embodiments, when the bonding wire 4 is obliquely connected to the pad disposed at an oblique position, it is possible to decrease the gap between the adjacent CMUT chips. However, in a case of a semiconductor sensor or the CMUT chip which needs to secure a distance from a pad to a chip end portion, a connection method of the bonding wire 4 in the third embodiment shown in FIG. 10 may be employed.

In addition, when the ultrasound images are joined together and formed, it is desirable that the distance between the drive electrode 3f of the CMUT chip 2a and the drive electrode 3q of the CMUT chip 2b is an integral multiple of the width U of the drive electrode 3. In the third embodiment, as shown in FIG. 10, the distance between the drive electrode 3f of the CMUT chip 2a and the drive electrode 3q of the CMUT chip 2b is three times the width U.

Fourth Embodiment

FIG. 11 is a top view of a region in which the CMUT chips 2a and 2b are adjacent to each other in the fourth embodiment.

The top view in FIG. 11 shows a relationship between the adjacent CMUT chips 2a and 2b, the pad 32, and the bonding wires 4. The CMUT chip 2a has a rectangular shape, the pad 32 for providing an electrical connection to the outside is disposed on the upper side and the right side, and a pad 38 for providing an electrical connection to the outside is disposed on the lower side and the left side. The pad 32 is electrically connected to the CMUT element portion 21a via the crank-shaped internal wiring 31. The pad 38 is electrically connected to the CMUT element portion 21a via a crank-shaped internal wiring 37. The crank-shaped internal wiring 31 is wired to be oblique with respect to each side of the CMUT chip 2a. The crank-shaped internal wiring 37 is wired to be more oblique than the internal wiring 31, with respect to each side of the CMUT chip 2a. The CMUT chip 2b is also configured to be similar to the CMUT chip 2a.

The pad 32 of the CMUT chip 2a and the pad 38 of the CMUT chip 2b that is adjacent to the CMUT chip 2a are connected via the bonding wire 4. Connection will be described in detail in FIG. 12 to be described below.

FIG. 12 is an enlarged top view of a region in which the CMUT chips 2a and 2b are adjacent to each other in the fourth embodiment.

The pads 32f to 32i are connected to drive electrodes 3f to 3i via the internal wirings 31f to 31i, respectively. The pads 38p to 38s are connected to drive electrodes 3p to 3s via internal wirings 37p to 37s, respectively. The pads 32f to 32i and the pads 38p to 38s are electrically connected to each other, respectively, via the bonding wires 4f to 4i.

That is, the pad 32f is connected to the pad 38q further on the lower side by skipping the pad 32p disposed on an obliquely lower right side. The pad 32g is connected to the pad 38r further on the lower side by skipping the pad 32q disposed on an obliquely lower right side. This is an effective method in a case where the length E1 of the bonding wire 4 has to be far longer than the length B1 of the bonding wire 4 of the first embodiment.

In addition, when the ultrasound images are joined together and formed, it is desirable that the distance between the drive electrode 3f of the CMUT chip 2a and the drive electrode 3q of the CMUT chip 2b is an integral multiple of the width U of the drive electrode 3. In the fourth embodiment, as shown in FIG. 12, the distance between the drive electrode 3f of the CMUT chip 2a and the drive electrode 3q of the CMUT chip 2b is twice the width U. Here, the CMUT chips 2a and 2b are disposed to be separated by a chip gap E.

Fifth Embodiment

FIG. 13 is an enlarged sectional view of a region in which the CMUT chips 2a and 2b are adjacent to each other in the fifth embodiment.

The sectional view shows a relationship between the adjacent CMUT chips 2a and 2b, the pads 32, and the bonding wires 4. The CMUT chip 2a includes the CMUT element portion 21a on an inner side (left side on the paper surface) thereof, and pads 32a for providing an electrical connection are disposed on a peripheral portion (right side on the paper surface) of the CMUT chip. The pad 32a is electrically connected to the drive electrode 3 of the CMUT element portion 21a via an internal wiring 31a.

The CMUT chip 2b includes the CMUT element portion 21b on an inner side (right side on the paper surface) thereof, and a pad 32b for providing an electrical connection to the outside is disposed on a peripheral portion (the right side on the paper surface) of the CMUT element portion. The pad 32b is electrically connected to the drive electrode 3 of the CMUT element portion 21b via an internal wiring 31b.

The pad 32a of the CMUT chip 2a and the pad 32b of the CMUT chip 2b that is adjacent to the CMUT chip 2a are electrically connected via the bonding wire 4. Since the pad 32b of the CMUT chip 2b in the fifth embodiment is disposed at a lower position than the pad 32a of the CMUT chip 2b, it is possible to secure a length of the bonding wire 4.

Sixth Embodiment

FIG. 14 is an enlarged sectional view of a region in which the CMUT chips 2a and 2b are adjacent to each other in the sixth embodiment.

The sectional view shows a relationship between the adjacent CMUT chips 2a and 2b, the pads 32, and the bonding wires 4. The CMUT chip 2a includes the CMUT element portion 21a on an inner side (the left side on the paper surface) thereof, and the pads 32a for providing the electrical connection are disposed sideways on the peripheral portion (the lower right side on the paper surface). The pad 32a is electrically connected to the drive electrode 3 of the CMUT element portion 21a via the internal wiring 31a.

The CMUT chip 2b includes the CMUT element portion 21b on an inner side (right side on the paper surface) thereof, and the pad 32b for providing an electrical connection to the outside is disposed sideways on the peripheral portion (right side on the paper surface). The pad 32b is electrically connected to the drive electrode 3 of the CMUT element portion 21b via the internal wiring 31b.

The pad 32 of the CMUT chip 2a and the CMUT chip 2b, which is adjacent to the CMUT chip 2a, are electrically connected to each other via the bonding wire 4. Since the pad 32b of the CMUT chip 2b in the sixth embodiment is disposed at a higher position than the pad 32a of the CMUT chip 2a, it is possible to secure the length of the bonding wire 4, similarly to the sixth embodiment.

Seventh Embodiment

FIG. 15 is a perspective view in the vicinity of the CMUT chips 2a to 2j arranged in a grid shape with two columns in the seventh embodiment.

The CMUT chips 2a to 2j are disposed in two columns of a chip column 22a and a chip column 22b. The CMUT chips 2a to 2e constituting the chip column 22a and the CMUT chips 2f to 2j constituting the chip column 22b are electrically connected via the bonding wire 6. Adjacent chips of the CMUT chips 2a to 2e in the chip column 22a are electrically connected to each other via the bonding wire 4. Adjacent chips of the CMUT chips 2f to 2j in the chip column 22b are electrically connected to each other via the bonding wire 4.

In other words, the CMUT chips 2a to 2j are electrically connected to each other via the bonding wire 4 and the bonding wire 6. One column of drive electrodes 3 connected via the bonding wire 4 and one row of drive electrodes 3 connected via the bonding wire 6 are in conjunction and can drive membranes of the CMUT. As described above, the chip columns 22a and 22b which each include five chips are arrayed to two columns in the grid shape, and thereby it is possible to provide the ultrasound probe 1 including the ultrasound transmitting/receiving surface having a wider area than that in the first embodiment shown in FIG. 4. Since a diagnosis range is widened in the ultrasound probe 1, it is possible to detect the ultrasound information in high definition at once.

Eighth Embodiment

FIG. 16 is a perspective view in the vicinity of CMUT chips 2a to 2o arranged in a grid shape with three columns in the eighth embodiment.

The CMUT chips 2a to 2o are disposed in the grid shape with three columns of chip columns 22a to 22c. The CMUT chips 2a to 2e constituting the chip column 22a and the CMUT chips 2f to 2j constituting the chip column 22b are electrically connected via the bonding wire 6. The CMUT chips 2f to 2j constituting the chip column 22b and the CMUT chips 2k to 2o constituting the chip column 22c are electrically connected via the bonding wire 6.

As described above, the chip columns 22a to 22c are arrayed to three columns in the grid shape, and thereby it is possible to perform sensing over a far wider range at once than the seventh embodiment shown in FIG. 15.

Modification Examples

The present invention is not limited to the embodiments described above and includes various modification examples. For example, the embodiments described above are described in detail for easy understanding of the invention, and the invention is not limited to including the entire configurations described above. It is possible to replace a part of a configuration of an embodiment with a configuration of another embodiment, and it is possible to add a configuration of an embodiment to a configuration of another embodiment. In addition, it is possible to add, remove, or replace a part of each of the configurations of the embodiments to, from, or with another configuration.

In the embodiments described above, control wires or information wires are shown when the wires are considered to be necessary for description, and all of the control wires or the information wires are not shown in a product. Actually, almost all of the configurations may be considered to be connected to each other.

In the ultrasound probe 1 of the embodiments described above, the CMUT chips 2 are disposed in one column, two columns, and three columns; however, the number of columns is not limited thereto, and the CMUT chips may be disposed in any number of columns. In addition, in the embodiments shown in FIGS. 4, 15, and 16, five CMUT chips 2 are aligned; however, the disposition is not limited thereto, and any number of CMUT chips may be disposed.

In the present invention, the plurality of CMUT chips are disposed in one or a plurality of columns, and this is not limited to the CMUT chips, but this may be effective for the semiconductor sensor chips. When a pad is connected to a pad in the oblique direction in a case where the pads between the adjacent semiconductor sensor chips are connected to each other via the bonding wire, it is possible to secure the length of the bonding wire. Therefore, it is possible to narrow the gap between the adjacent chips, and it is possible to reduce an installation area of the plurality of semiconductor sensor chips.

The semiconductor sensor chips and the CMUT chips are manufactured by using a semiconductor manufacturing process; however, a size of the chip influences the yield ratio. A defect occurs at any position of a wafer in the semiconductor manufacturing process. In a case where a plurality of defects are scattered in a wafer surface, an area of the chip increases, and a total number of chips acquired from one wafer decreases, and thus a defect rate increases. For example, in a case where 100 chips are acquired from an eight-inch wafer, and defects are scattered at five positions, the rest of 95 chips are good products, and a good product rate is 95%. On the other hand, in a case where 500 chips are acquired from an eight-inch wafer, and defects are scattered at five positions, 495 chips are good products, and a good product rate is 99%. Hence, as the chip size decreases, the yield ratio is improved.

In addition, a merit obtained when the small chips are aligned as described in the present invention is described. A wafer manufactured in the semiconductor process has a distribution in a surface due to properties or a film thickness of a deposited film. In the CMOS sensor, detection sensitivity is different depending on a cut-out position from the wafer surface. The CMUT chip has variation in the wafer surface, due to a height of a cavity interposed between two upper and lower electrodes. In a case of the CMUT, the upper and lower electrodes correspond to a drive electrode and a fixed electrode, respectively, applies a direct current voltage, and causes a membrane on a side of the drive electrode to be bent. In this state, an AC voltage is applied and the membrane on the side of the drive electrode is vibrated such that the ultrasound is generated. Therefore, the height of the cavity is important for the characteristics of the CMUT element. Hence, it is possible to measure the height of the cavity with capacitance of the upper and lower electrodes. Further, it is also possible to evaluate the height of the cavity with the maximum value of the capacitance obtained when sweeping application of the voltage is performed. Therefore, the capacitance is measured, variation in the CMUT chips is measured, and the CMUT chips having approximate capacitance characteristics are selected and arranged, and thereby it is possible to provide a CMUT chip array.

The chips have different characteristics due to variation in the wafer surface of the CMOS sensor or the CMUT chip, in some cases. In such a case, the chips having approximate characteristics may be selected and disposed by using a method of aligning and connecting the plurality of chips of the present invention. Consequently, it is possible to provide stable characteristics as one sensor. In addition, the variation described above is not limited to the variation in the wafer surface and can also be applied to each batch or lot of wafers.

Further, the present invention is applied, and thereby the CMUT chips having drive frequency characteristics are aligned and disposed such that it is possible to transmit and receive ultrasound having different frequencies simultaneously. Thus, the present invention is applicable to a two-wavelength diagnosis or the like.

In addition, according to the present invention, small chips are aligned, and thereby it is possible to replace large chips with the aligned small chips. Therefore, it is possible to improve the yield ratio of a measuring instrument or the ultrasound probe by using the semiconductor sensor chips or the CMUT chips.

REFERENCE SIGNS LIST

1: ultrasound probe
11: backing 2, 2a to 2o: CMUT chip
21, 21a to 21e: CMUT element portion
22a to 22c: chip column
3, 3e to 3j, 3p to 3u: drive electrode (sensor cell)
32, 34, 36, 38: pad
31, 33, 35, 37: internal wiring
4, 6: bonding wire
71: flexible board
72: connector
73: circuit board
74: connection terminal
75: acoustic lens
8: ultrasound diagnostic apparatus
81: control panel
82: ultrasound transmitting/receiving unit
821: ultrasound pulse generator
822: converter
83: ultrasound image forming unit
84: control unit
85: display unit
9: subject

The invention claimed is:

1. An ultrasound diagnostic apparatus comprising:
an ultrasound probe that includes:
a first semiconductor sensor chip that is provided with an element portion in which first sensor cells are arranged; and
a second semiconductor sensor chip that is provided with an element portion in which second sensor cells are arranged, the second semiconductor sensor chip being adjacent to the first semiconductor sensor chip and having an electric connection via a bonding wire between each of the second sensor cells and an adjacent first sensor cell of the first semiconductor sensor chip, respectively,
wherein the bonding wire is wired in an oblique direction on sides of the adjacent first and second semiconductor sensor chips.

2. The ultrasound diagnostic apparatus according to claim 1,
wherein, with respect to a first pad of the first semiconductor sensor chip, a second pad of the second semiconductor sensor chip, which is electrically connected to the first pad of the first semiconductor sensor chip, is disposed in an oblique direction to the sides of the adjacent first and second semiconductor sensor chips.

3. The ultrasound diagnostic apparatus according to claim 1,
wherein, with respect to each first sensor cell of the first semiconductor sensor chip, a pad of the corresponding first sensor cell is disposed in an oblique direction to the sides of the adjacent first and second semiconductor sensor chips.

4. The ultrasound diagnostic apparatus according to claim 3,
wherein, with respect to each second sensor cell of the second semiconductor sensor chip, a pad of the corresponding second sensor cell is disposed in an oblique direction to the sides of the adjacent first and second semiconductor sensor chips.

5. An ultrasound diagnostic apparatus comprising:
an ultrasound probe that includes:
a first semiconductor sensor chip that is provided with an element portion in which first sensor cells are arranged; and
a second semiconductor sensor chip that is provided with an element portion in which second sensor cells are arranged, the second semiconductor sensor chip being adjacent to the first semiconductor sensor chip and having an electric connection via a bonding wire between each of the second sensor cells and an adjacent first sensor cell of the first semiconductor sensor chip, respectively,
wherein the bonding wire is wired in an oblique direction with respect to an arranging direction of the first and second semiconductor sensor chips.

6. A semiconductor sensor chip array comprising:
backing;
a plurality of the semiconductor sensor chips, which are arranged on the backing; and
a wire bonding for electrically connecting pads to each other, the pads being connected to adjacent columns of sensor cells in the semiconductor sensor chips,
each semiconductor sensor chip comprising:
an element portion in which sensor cells are arranged in a grid shape within a rectangle; and
a pad that is electrically connected to each of the sensor cells which are positioned on one side of the element portion and is positioned to be oblique with respect to an arranging direction of the sensor cells.

7. The semiconductor sensor chip array according to claim 6,
wherein the plurality of semiconductor sensor chips are disposed in one line.

8. The semiconductor sensor chip array according to claim 6,
wherein the plurality of semiconductor sensor chips are disposed in a grid shape.

* * * * *